(12) United States Patent
Despres, III et al.

(10) Patent No.: US 7,097,664 B2
(45) Date of Patent: *Aug. 29, 2006

(54) MODULAR FEMORAL STEM COMPONENT FOR A HIP JOINT PROSTHESIS

(75) Inventors: Alfred S. Despres, III, Shingle Springs, CA (US); Daniel E. E. Hayes, Jr., Placerville, CA (US)

(73) Assignee: Depuy Products, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/764,831

(22) Filed: Jan. 26, 2004

(65) Prior Publication Data

US 2004/0243248 A1 Dec. 2, 2004

Related U.S. Application Data

(63) Continuation of application No. 09/909,923, filed on Jul. 20, 2001, now Pat. No. 6,682,568.

(60) Provisional application No. 60/219,955, filed on Jul. 20, 2000, provisional application No. 60/219,963, filed on Jul. 20, 2000.

(51) Int. Cl.
A61F 2/32 (2006.01)

(52) U.S. Cl. .................................. 623/22.42

(58) Field of Classification Search ............. 623/23.15, 623/23.18, 23.21, 23.22, 23.23, 23.25, 23.42, 623/23.44, 23.46, 22.42, 23.43, 22.45
See application file for complete search history.

(56) References Cited

U.S. PATENT DOCUMENTS

| | | | |
|---|---|---|---|
| 3,848,272 A * | 11/1974 | Noiles ..................... | 623/23.22 |
| RE28,895 E | 7/1976 | Noiles | |
| 4,355,429 A * | 10/1982 | Mittelmeier et al. ..... | 623/20.14 |
| 4,520,511 A | 6/1985 | Gianezio et al. | |
| 4,790,852 A * | 12/1988 | Noiles ..................... | 623/23.46 |
| 4,846,839 A * | 7/1989 | Noiles ..................... | 623/23.46 |
| 4,851,007 A * | 7/1989 | Gray ........................ | 623/22.46 |
| 4,878,917 A | 11/1989 | Kranz et al. | |
| 4,936,853 A * | 6/1990 | Fabian et al. ............. | 623/20.15 |
| 5,080,685 A * | 1/1992 | Bolesky et al. ........... | 623/22.42 |
| 5,108,452 A * | 4/1992 | DeMane et al. .......... | 623/22.42 |
| 5,156,624 A * | 10/1992 | Barnes ..................... | 623/22.45 |
| 5,181,928 A * | 1/1993 | Bolesky et al. ........... | 623/22.42 |
| 5,286,260 A * | 2/1994 | Bolesky et al. ........... | 623/22.42 |
| 5,370,706 A * | 12/1994 | Bolesky et al. ........... | 623/23.44 |
| 5,507,830 A * | 4/1996 | DeMane et al. .......... | 623/22.42 |
| 5,540,694 A * | 7/1996 | DeCarlo, Jr. et al. ...... | 606/80 |
| 5,725,592 A * | 3/1998 | White et al. .............. | 623/23.35 |
| 5,766,255 A * | 6/1998 | Slamin et al. ............ | 623/20.15 |
| 5,782,921 A * | 7/1998 | Colleran et al. .......... | 623/20.15 |
| 5,876,459 A * | 3/1999 | Powell ..................... | 623/23.15 |
| 5,902,340 A * | 5/1999 | White et al. .............. | 128/898 |
| 5,906,644 A * | 5/1999 | Powell ..................... | 623/20.15 |
| 6,102,956 A * | 8/2000 | Kranz ...................... | 623/23.15 |
| 6,139,584 A | 10/2000 | Ochoa et al. | |
| 6,264,699 B1 * | 7/2001 | Noiles et al. ............. | 623/23.23 |
| 6,299,648 B1 * | 10/2001 | Doubler et al. ........... | 623/23.18 |
| 6,319,286 B1 * | 11/2001 | Fernandez et al. ........ | 623/23.18 |
| 6,355,069 B1 | 3/2002 | DeCarlo, Jr. et al. | |
| 2002/0072799 A1 * | 6/2002 | Despres et al. ........... | 623/16.11 |

* cited by examiner

*Primary Examiner*—Eduardo C. Robert
(74) *Attorney, Agent, or Firm*—Pandiscio & Pandiscio

(57) ABSTRACT

A prosthetic femoral stem component comprising a body element, a neck element and a stem element, with the body element, neck element and stem element being secured to one another with a modular connection, wherein the modular connection comprises a taper junction and an engaged-fit junction.

10 Claims, 5 Drawing Sheets

MODULAR FEMORAL STEM COMPONENT FOR A HIP JOINT PROSTHESIS

REFERENCE TO PENDING PRIOR PATENT APPLICATIONS

This is a continuation of prior U.S. patent application Ser. No. 09/909,923, filed Jul. 20, 2001 now U.S. Pat. No. 6,682,568, by Alfred S. Despres III et al. for MODULAR FEMORAL STEM COMPONENT FOR A HIP JOINT PROSTHESIS which in turn claims benefit of (1) prior U.S. Provisional Patent Application Ser. No. 60/219,955, filed Jul. 20, 2000 by Alfred S. Despres III et al. for MODULAR ORTHOPEDIC CONNECTION; and (2) prior U.S. Provisional Patent Application Ser. No. 60/219,963, filed Jul. 20, 2000 by Alfred S. Despres III et al. for FORCE COUPLE CONNECTION. The three above-identified patent applications are hereby incorporated herein by reference

FIELD OF THE INVENTION

This invention relates to surgical apparatus and procedures in general, and more particularly to orthopedic prostheses for restoring the hip joint.

BACKGROUND OF THE INVENTION

Joint replacement surgery seeks to replace portions of a joint with prosthetic components so as to provide long-lasting function and pain-free mobility.

For example, in the case of a prosthetic total hip joint, the head of the femur is replaced with a prosthetic femoral stem component, and the socket of the acetabulum is replaced by a prosthetic acetabular cup component, whereby to provide a prosthetic total hip joint.

In the case of a prosthetic total knee joint, the top of the tibia is replaced by a prosthetic tibial component, and the bottom of the femur is replaced by a prosthetic femoral component, whereby to provide a prosthetic total knee joint.

The present invention is directed to orthopedic prostheses for restoring the hip joint and, more particularly, to improved prosthetic femoral stem components.

Prosthetic femoral stem components typically comprise a proximal section for seating in the proximal section of the resected femur and presenting a ball for seating in the acetabular socket, and a distal section for seating in the femur's medullary canal so as to extend along the shaft of the femur.

It is, of course, important that the prosthetic femoral stem component make a proper fit with the surrounding bone. To this end, prosthetic femoral stem components are typically offered in ranges of different sizes in an effort to accommodate variations in patient anatomy. However, despite this, it has been found that it can be difficult to provide the correct prosthetic femoral stem component for patients. This is due to the wide variation in patient anatomies and to the practical limitations of hospital inventory. By way of example, where a femoral component is selected having a proximal section appropriately sized for the proximal section of the resected femur, the distal section of the prosthesis may not be appropriately sized for proper seating in the distal section of the femur. This can present serious problems for the patient, including problems relating to joint stability and pain.

On account of the foregoing, there has been substantial interest in forming prosthetic femoral stem components out of a plurality of separate elements, wherein each of the elements may be independently selected so as to most closely approximate patient anatomy, and wherein the separate elements may be assembled to one another in situ, using modular connections, so as to provide the best possible prosthetic femoral stem component for the patient.

Once deployed in the patient's body, the prosthetic femoral stem component, and hence the modular connections securing the separate elements to one another, are subjected to axial, bending and torsional loads. While different types of modular connections are known in the art, no one modular connection is ideal for dealing with all three types of loads, i.e., axial, bending and torsional loads. By way of example, taper connections generally accommodate axial (i.e., compressive) loads well, but they generally do not accommodate bending and torsional loads particularly well. By way of further example, concentric cylinder connections generally accommodate bending loads well, but they generally do not accommodate axial and torsional loads particularly well.

SUMMARY OF THE INVENTION

As a result, one object of the present invention is to provide an improved modular connection for connecting together a plurality of separate elements so as to form a prosthetic femoral stem component.

Another object of the present invention is to provide an improved prosthetic femoral stem component.

And another object of the present invention is to provide an improved prosthetic total hip joint.

Still another object of the present invention is to provide an improved method for restoring a hip joint.

These and other objects are addressed by the provision and use of the present invention.

In one form of the invention, there is provided an improved modular connection for connecting together a plurality of separate elements so as to form a prosthetic femoral stem component, the improved modular connection comprising, in combination, a taper junction and an engaged-fit junction.

In another form of the invention, there is provided an improved prosthetic femoral stem component comprising a body element, a neck element and a stem element, with the body element, neck element and stem element being secured to one another with a modular connection, wherein the modular connection comprises, in combination, a taper junction and an engaged-fit junction.

In another form of the invention, there is provided an improved prosthetic total hip joint comprising a prosthetic femoral stem component and a prosthetic acetabular cup component, wherein the femoral stem component comprises a body element, a neck element and a stem element, with the body element, neck element and stem element being secured to one another with a modular connection, wherein the modular connection comprises, in combination, a taper junction and an engaged-fit junction.

In another form of the invention, there is provided an improved method for restoring a hip joint, wherein the method comprises the steps of: resecting the head of the femur and preparing the interior of the femur to receive a prosthetic femoral stem component; assembling a prosthetic femoral stem component comprising a body element, a neck element and a stem element by selecting appropriately sized elements and securing them together with a modular connection, wherein the modular connection comprises, in combination, a taper junction and an engaged-fit junction; and seating the prosthetic femoral stem component in the femur.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts and further wherein.

DETAILED DESCRIPTION OF THE PREFERRED EMBODIMENTS

Figure 1:
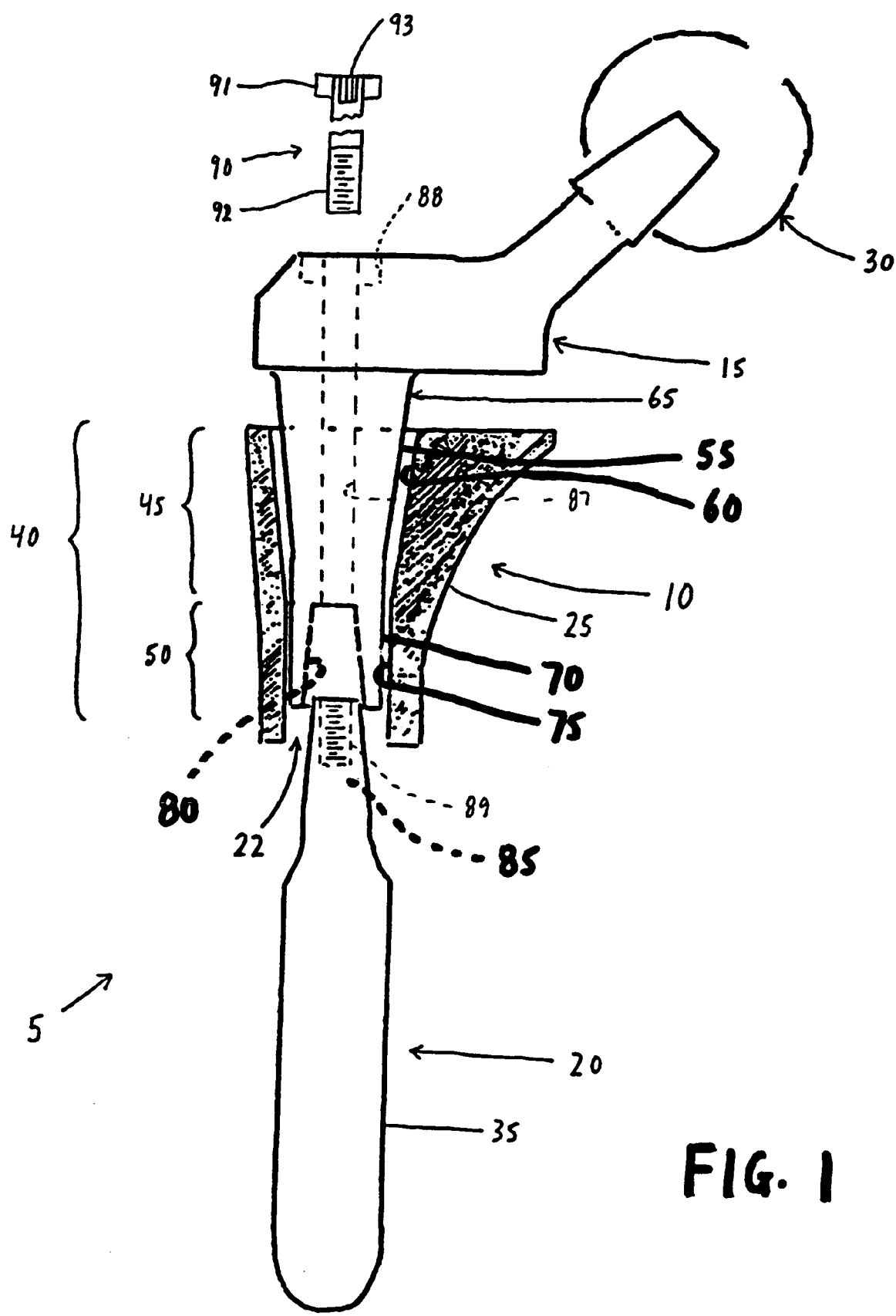
FIG. 1 is a schematic, exploded side view of a prosthetic femoral stem component formed in accordance with the present invention.

Looking first at FIG. 1, there is shown a prosthetic femoral stem component 5 formed in accordance with the present invention. Prosthetic femoral stem component 5 generally comprises a body element 10, a neck element 15 and a stem element 20. Body element 10 includes a central aperture 22 into which portions of neck element 15 and stem element 20 extend. Body element 10 is selected so that its outer surface 25 is properly sized to be seated in the proximal section of a resected femur. Neck element 15 is selected so that when it is mounted to the remainder of prosthetic femoral stem component 5 deployed within the femur, the neck element's ball 30 will be properly seated in the hip joint's corresponding acetabular cup. Stem 20 is selected so that its outer surface 35 is properly sized to be seated within the medullary canal of the femur.

In accordance with the present invention, body element 10, neck element 15 and stem element 20 are adapted to be secured to one another using an improved modular connection 40 so as to form the complete prosthetic femoral stem component 5.

More particularly, modular connection 40 comprises, in combination, two load-bearing junctions: a taper junction 45 and an engaged-fit junction 50.

Figure 2:
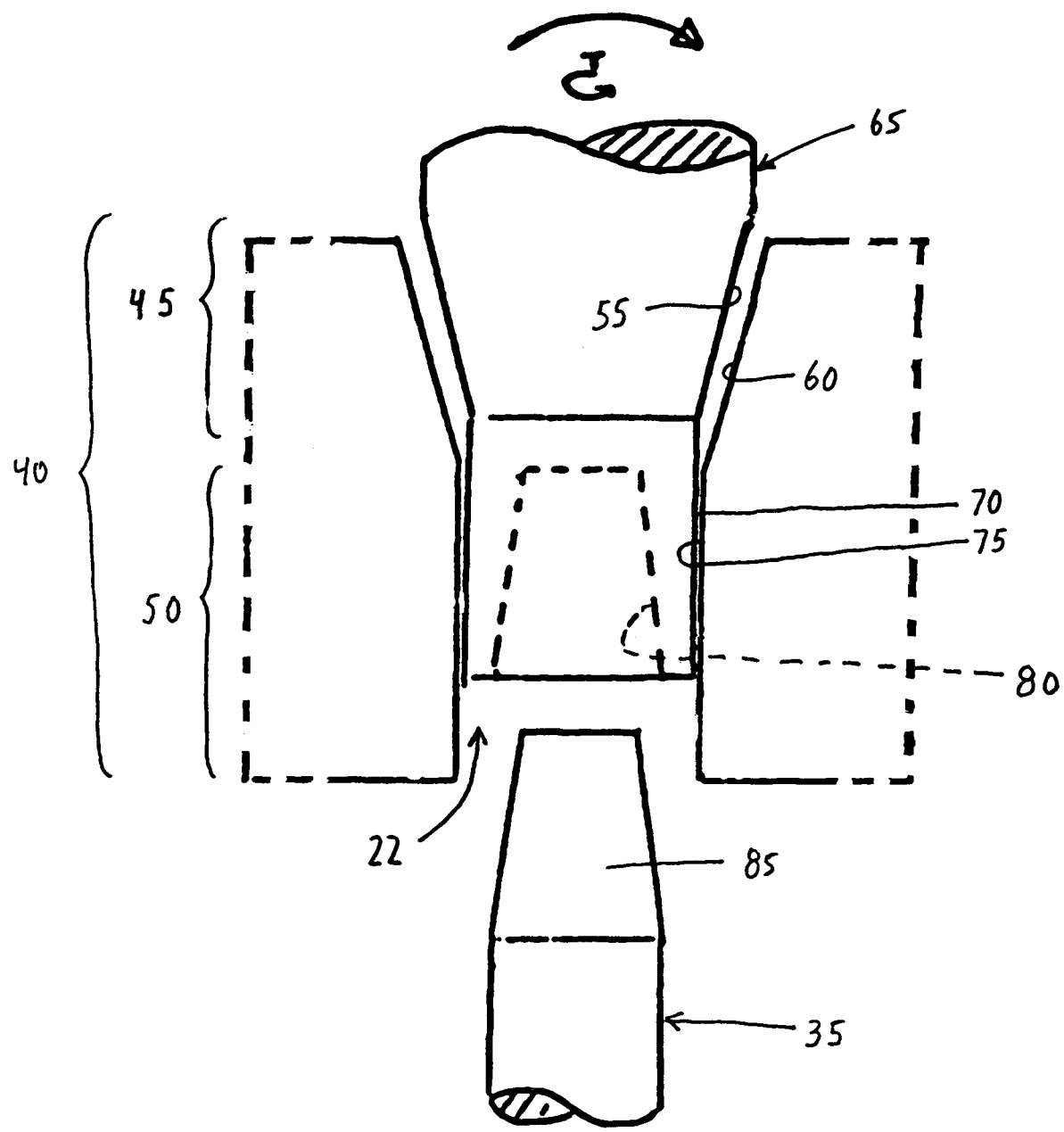
FIG. 2 is an enlarged, schematic, exploded side view of the modular connection used to form the prosthetic femoral stem component shown in FIG. 1.

Looking now at FIGS. 1 and 2, taper junction 45 is formed by the interaction of a first taper 55 with a corresponding second taper 60. More particulary, first taper 55 is formed on the shaft 65 of neck element 15. Second taper 60 is formed along a portion of the sidewall defining the body element's central aperture 22. First taper 55 and second taper 60 seat securely against one another so as to together form the load-bearing taper junction 45.

Still looking now at FIGS. 1 and 2, engaged-fit junction 50 is formed by the interaction of a first concentric wall 70 with a second concentric wall 75. More particularly, first concentric wall 70 is formed on shaft 65 of neck element 15. Preferably first concentric wall 70 is disposed on shaft 65 coaxial with, and distal to, first taper 55. Second concentric wall 75 is formed along a portion of the sidewall defining the body element's central aperture 22. Preferably second concentric wall 75 is disposed on body element 10 coaxial with, and distal to, second taper 60. First concentric wall 70 and second concentric wall 75 seat securely against one another so as to form the load-bearing engaged-fit junction 50.

In general, the engaged-fit junction 50 is a mechanical connection that achieves stability by the deformation of one member so that it is pressure locked against a constraining second member. This deformation can be expansion (e.g., as in a taper expanded collet) or contraction (e.g., as in a force fit). The deformation can also be effected by thermal expansion or thermal contraction (e.g., as with a shape memory alloy such as Nitinol or the like). Regardless of how the deformation is achieved, the resulting mechanical connection has surfaces which are forcefully engaged against one another as a result of the deformation, whereby to establish the engaged-fit junction.

As noted above, there are a number of ways in which first concentric wall 70 and second concentric wall 75 can be made to seat securely against one another so as to form the load-bearing engaged-fit junction 50.

For example, first concentric wall 70 can be made slightly oversized relative to second concentric wall 75, such that force fitting first concentric wall 70 internal to second concentric wall 75 will create the engaged-fit junction 50.

Alternatively, and in accordance with a preferred form of the present invention, the distal end of the neck element's shaft 65 may be formed with a recess 80, and the proximal end of stem element 20 may include a projection 85 for insertion into recess 80. More particularly, projection 85 is diametrically oversized relative to recess 80, such that insertion of projection 85 into recess 80 will cause a radial expansion of first concentric wall 70 into engagement with second concentric wall 75, whereby to create the engaged-fit junction 50. In one preferred form of the invention, recess 80 and projection 85 are both tapered, and the distal end of neck 15 is a split collet. Alternatively, the distal end of neck 15 may be formed out of a material sufficiently resilient to engage second concentric wall 75 without being split. If desired, a threaded bolt can thereafter lock stem element 20 to neck element 15. By way of example, neck element 15 can include a bore 87 and a counterbore 88, and stem element 20 can include a threaded bore 89. Then a bolt 90, having a head 91 and a distal thread 92, may be driven, via a recessed hex drive 93, so that its distal thread 92 seats in stem threaded bore 89 and its head 91 seats in neck counterbore 88, whereby to lock stem element 20 to neck element 15.

Due to the unique construction of modular connection 40, the prosthetic femoral stem component 5 is able to accommodate axial, bending and torsional loads better than prior art devices. More particularly, modular connection 40 simultaneously provides two load-bearing junctions: the taper junction 45 and the engaged-fit junction 50. The taper junction 45 accommodates axial (i.e., compressive) loads extremely well. At the same time, the engaged-fit junction 50 accommodates bending and torsional loads extremely well. Additionally, the engaged-fit junction 50 stabilizes the taper junction 45 against bending and torsional loads. Together, the two load-bearing junctions collectively handle axial, bending and torsional loads significantly better than prior art devices.

Figure 3:
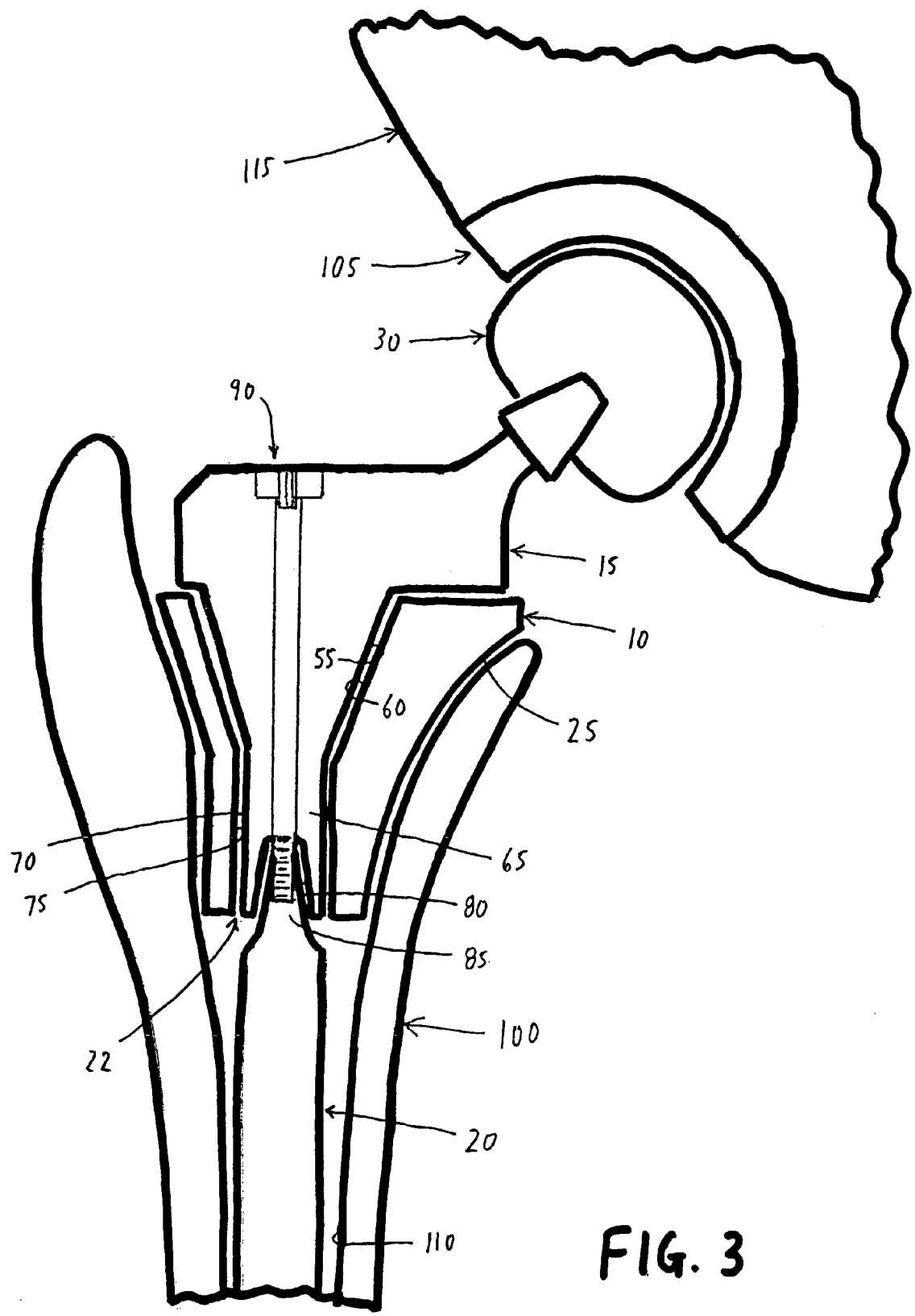
FIG. 3 is a schematic side view of a prosthetic total hip joint formed in accordance with the present invention.

Looking next at FIG. 3, prosthetic femoral stem component 5 is preferably used as follows.

First, the patient's femur 100 is prepared, e.g., by resecting the head of the femur, and clearing the interior of the femur to receive the prosthetic femoral stem component.

Next, a body element 10 is selected so that its outer surface 25 is properly sized to be seated in the proximal section of the resected femur. Then a neck element 15 is selected so that when it is mounted to the remainder of the prosthetic femoral stem component deployed within the femur, the neck element's ball 30 will be properly seated in the hip joint's corresponding acetabular cup 105. Then a stem 20 is selected so that its outer surface is properly sized to be seated within the medullary canal 110 of the femur.

Next, body element 10, neck element 15 and stem element 20 are assembled into the prosthetic femoral stem component 5. This is preferably done by passing the distal end of the neck element's shaft 65 down the body element's central aperture 22 until first taper 55 engages second taper 60, whereby to create the tapered junction 45 (FIGS. 1 and 2), and then passing the proximal end of stem element 20 up into central aperture 22 until the stem element's oversized projection 85 is inserted into recess 80, whereupon first concentric wall 70 will expand into engagement with second concentric wall 75, whereby to create the engaged-fit junction 50 (FIGS. 1 and 2). If desired, threaded bolt 90 can be used to lock system element 20 to neck element 15.

Next, prosthetic femoral stem component 5 is deployed in the resected femur, the acetabular side of the joint is prepared (i.e., prosthetic acetabular cup component 105 is deployed in the patient's acetabulum 115), ball 30 is set on neck element 15, and the hip is reduced.

Figure 4:
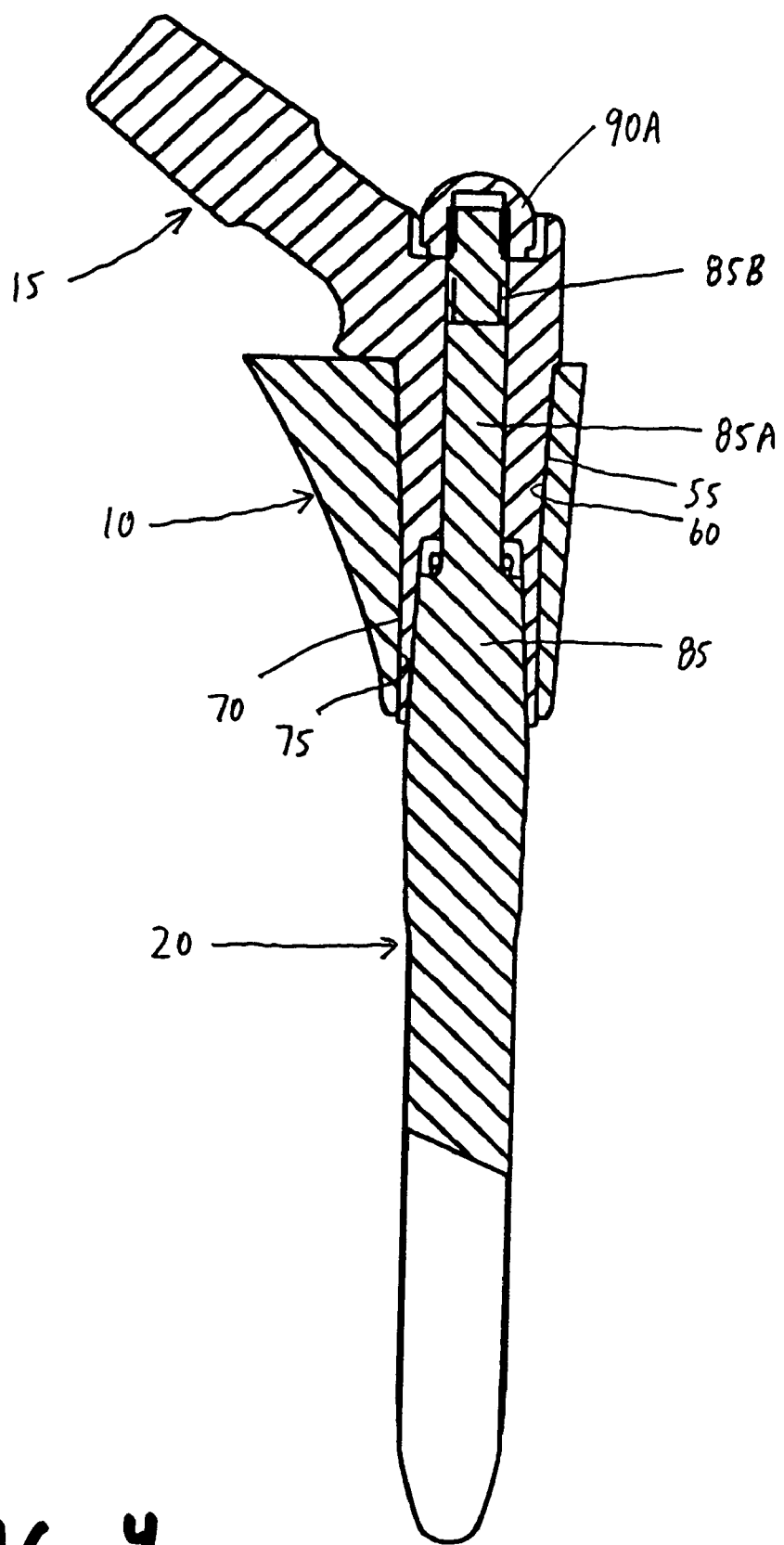
FIG. 4 is a schematic side view of another form of prosthetic femoral stem component formed in accordance with the present invention.
Figure 5:
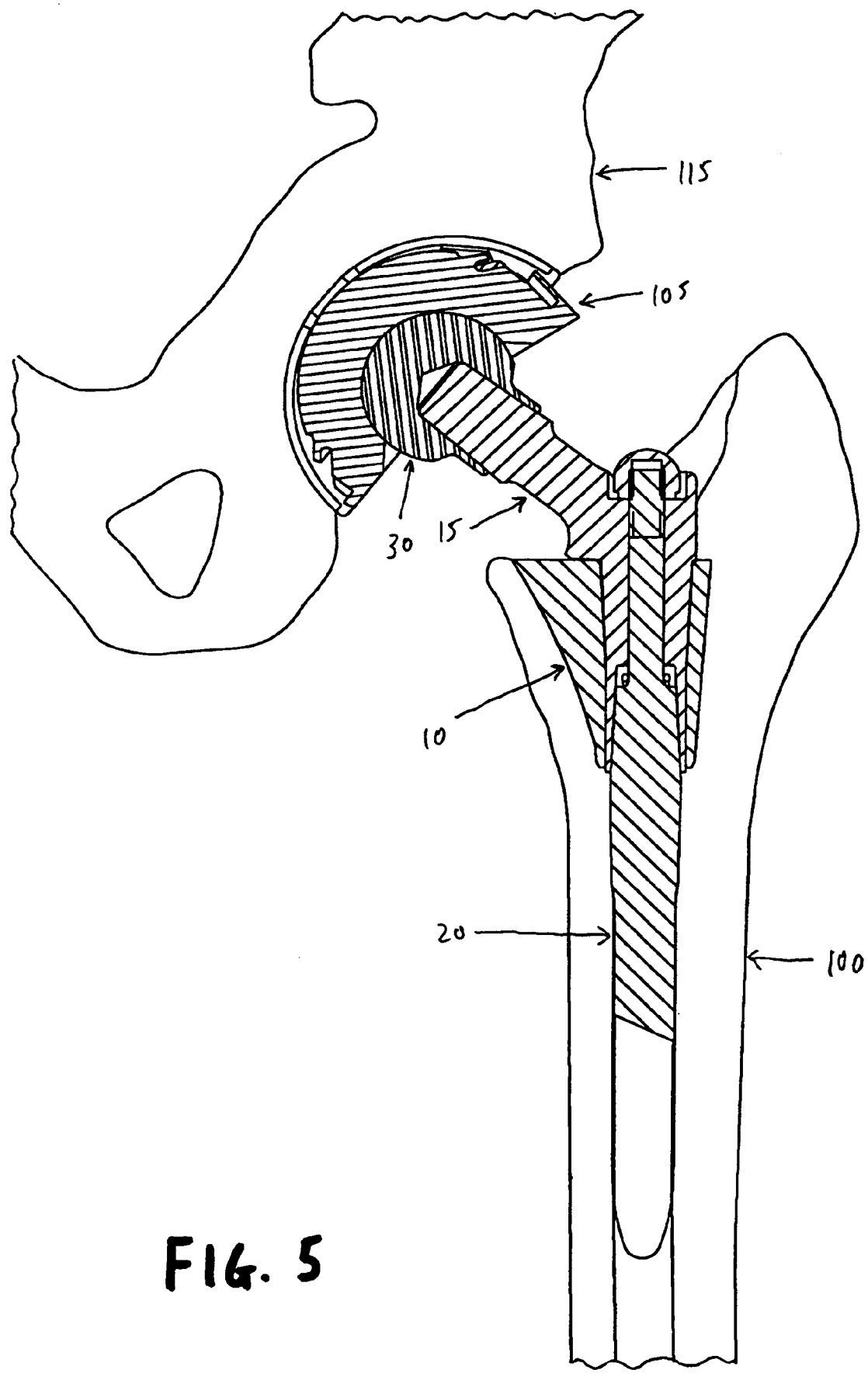
FIG. 5 is a sectional view of a prosthetic total hip joint using the prosthetic femoral stem component shown in FIG. 4.

As noted above, a bolt 90 can be passed down a bore 87 in neck element 15 and secured to stem element 20 as as to secure stem element 20 to neck element 15. Alternatively, other arrangements can also be used. Thus, for example, and looking now at FIGS. 4 and 5, stem element 20 can include a shaft 85A proximal to its projection 85, with the proximal end of shaft 85A including screw threads 85B, and with this shaft 85A being passed up through bore 87 in neck element 15. A nut 90A engages threads 85B and seats in the neck element's counterbore 88 to lock stem element 20 to neck element 15.

It will be understood that many additional changes in the details, materials, steps and arrangement of parts, which have been herein described and illustrated in order to explain the nature of the invention, may be made by those skilled the art without departing from the principles and scope of the present invention.

What is claimed is:

1. A prosthetic femoral stem component comprising a body element, a neck element and a stem element, with said body element, neck element and stem element being secured to one another with a modular connection, said modular connection comprising, in combination, a taper junction and an engaged-fit junction;
    said taper junction being formed by interaction of a first taper with a second taper, the first taper being formed on a shaft of said neck element, and the second taper being formed along a portion of a sidewall defining an aperture extending through said body element; and
    said engaged-fit junction being formed by interaction of a first concentric wall with a second concentric wall, with the first concentric wall being formed on the shaft of said neck element, and the second concentric wall being formed along a portion of the sidewall defining the aperture extending through said body element.

2. A prosthetic femoral stem component according to claim 1 wherein the first concentric wall is disposed on the shaft of said neck element coaxial with, and distal to, the first taper.

3. A prosthetic femoral stem component according to claim 2 wherein the second concentric wall is disposed on said body element coaxial with, and distal to, the second taper.

4. A modular connection for connecting together a plurality of separate elements so as to form a prosthetic femoral stem component, said modular connection comprising, in combination, a taper junction and an engaged-fit junction;
    said engaged-fit junction being formed by interaction of a first concentric wall with a second concentric wall;
    the first concentric wall being located internally of the second concentric wall; and
    the first concentric wall being deformable so as to be pressure locked against the second concentric wall.

5. A modular connection according to claim 4 wherein the first concentric wall is radially expandable so as to be pressure locked against the second concentric wall.

6. A modular connection according to claim 5 wherein the first concentric wall is formed on a shaft of a neck element, and the second concentric wall is formed along a portion of a sidewall defining an aperture extending through a body element, and further wherein the first concentric wall is radially expandable by insertion of a stem element into a recess formed in the neck element.

7. A prosthetic femoral stem component comprising a body element, a neck element and a stem element, with said body element, neck element and stem element being secured to one another with a modular connection, wherein said modular connection comprises, in combination, a taper junction and an engaged-fit junction;
    wherein said engaged-fit junction is formed by interaction of a first concentric wall with a second concentric wall;
    wherein the first concentric wall is located internally of the second concentric wall; and
    wherein the first concentric wall is deformable so as to be pressure locked against the second concentric wall.

8. A prosthetic femoral stem component according to claim 7 wherein the first concentric wall is radially expandable so as to be pressure locked against the second concentric wall.

9. A prosthetic femoral stem component according to claim 8 wherein the first concentric wall is formed on a shaft of said neck element, and the second concentric wall is formed along a portion of a sidewall defining an aperture extending through said body element, and further wherein the first concentric wall is radially expandable by insertion of said stem element into a recess formed in said neck element.

10. A prosthetic femoral stem component comprising a body element, a neck element and a stem element, with said body element, neck element and stem element being secured to one another with a modular connection, the modular connection comprising, in combination, a taper junction and an engaged-fit junction;
    wherein said engaged-fit junction is formed by interaction of a first concentric wall with a second concentric wall; and
    wherein the first concentric wall is formed on a shaft of said neck element, and the second concentric wall is formed along a portion of a sidewall defining an aperture extending through said body element.

* * * * *